(12) United States Patent
Hands

(10) Patent No.: US 6,861,853 B2
(45) Date of Patent: Mar. 1, 2005

(54) INVESTIGATING CORROSION

(75) Inventor: Brian Hands, Seascale (GB)

(73) Assignee: British Nuclear Fuels plc, Risley (GB)

(*) Notice: Subject to any disclaimer, the term of this patent is extended or adjusted under 35 U.S.C. 154(b) by 0 days.

(21) Appl. No.: 10/221,259

(22) PCT Filed: Mar. 6, 2001

(86) PCT No.: PCT/GB01/00951
§ 371 (c)(1),
(2), (4) Date: Jan. 28, 2003

(87) PCT Pub. No.: WO01/70003

PCT Pub. Date: Sep. 27, 2001

(65) Prior Publication Data
US 2003/0184321 A1 Oct. 2, 2003

(30) Foreign Application Priority Data
Mar. 14, 2000 (GB) .............................................. 0005946

(51) Int. Cl.$^7$ .............................................. G01R 27/26
(52) U.S. Cl. ...................................... 324/700; 324/71.1
(58) Field of Search ........................ 204/404; 324/452, 324/456, 529, 700, 71.1; 422/53

(56) References Cited

U.S. PATENT DOCUMENTS

| 1,895,643 | A | 1/1933 | Putnam | |
|---|---|---|---|---|
| 3,853,730 | A | 12/1974 | Anderson | 204/196.06 |
| 4,019,133 | A | 4/1977 | Manley et al. | |
| 4,087,476 | A | 5/1978 | Hayes | 324/229 |

(List continued on next page.)

FOREIGN PATENT DOCUMENTS

| EP | 0 150 552 A1 | 8/1985 |
|---|---|---|
| EP | 0 224 230 A3 | 6/1987 |
| EP | 0 344 576 A2 | 12/1989 |
| GB | 365 555 | 1/1932 |
| WO | WO 83/03675 | 10/1983 |
| WO | WO 90/04779 | 5/1990 |
| WO | WO 94/09354 | 4/1994 |
| WO | WO 01/69223 A2 | 9/2001 |
| WO | WO 01/70003 A2 | 9/2001 |

OTHER PUBLICATIONS

A. Daaland, *Modelling of Local Corrosion Attacks on a Plate Geometry for Developing the FSM Technology*, Insight, vol. 38, No. 12, Dec. 1996, pp. 872–875.

Roe D. Strommen, et al., *FSM–A Unique Method for Monitoring Corrosion of Steel Piping and Vessels*, Material Performance, vol. 32, No. 3, Mar. 1993, pp. 50–55.

R. Johnson, et al., *Weld Root Corrosion Monitoring with a New Electrical Field Signature Mapping Inspection Tool*, Corrosion 2000, 'Online', Mar. 26–31, 2000, XP002187933.

(List continued on next page.)

*Primary Examiner*—N. Le
*Assistant Examiner*—Walter Benson
(74) *Attorney, Agent, or Firm*—Workman Nydegger

(57) ABSTRACT

A method of investigating corrosion includes providing a mounting unit for two or more electrical contacts, introducing the mounting unit to a replica of a location which has not corroded, measuring the voltage between the two or more electrical contacts at one or more times, the two or more electrical contacts being in contact with the replica of the location being investigated, introducing the mounting unit to the location which may have corroded, measuring the voltage between and/or the variation in the voltage between two or more electrical contacts at a first time and at one or more other times, the two or more electrical contacts being in contact with the location being investigated, passing a current through the replica location at the time of the voltage measurement and through the location at the time of the voltage measurements, the voltage measurements for the location indicating the extent of corrosion.

24 Claims, 1 Drawing Sheet

U.S. PATENT DOCUMENTS

| | | | |
|---|---|---|---|
| 4,087,749 A | 5/1978 | McCormack | 324/225 |
| 4,096,437 A | 6/1978 | Kitzinger et al. | 324/227 |
| 4,328,462 A | 5/1982 | Jensen | 324/229 |
| 4,338,097 A | 7/1982 | Turner et al. | 436/6 |
| 4,338,563 A | 7/1982 | Rhoades et al. | 324/700 |
| 4,419,892 A | 12/1983 | Goolsby et al. | |
| 4,591,792 A | 5/1986 | Birchmeier et al. | 324/425 |
| 4,642,557 A | 2/1987 | Ross | 324/71.2 |
| 4,703,253 A | 10/1987 | Strommen | 324/700 |
| 4,814,705 A | 3/1989 | Saunderson | 324/225 |
| 4,821,204 A | 4/1989 | Hüschelrath | 702/38 |
| 4,982,154 A | 1/1991 | Schwabe et al. | 324/761 |
| 5,126,654 A | 6/1992 | Murphy et al. | 324/71.2 |
| 5,165,794 A | 11/1992 | Ortiz | 374/73 |
| 5,171,517 A | 12/1992 | Solomon et al. | 324/245 |
| 5,217,304 A | 6/1993 | Ortiz | 374/143 |
| 5,404,104 A | 4/1995 | Rivola et al. | 205/776.5 |
| 5,481,198 A | 1/1996 | Patel | 324/700 |
| 5,486,767 A | 1/1996 | Schwabe et al. | 324/715 |
| 5,581,037 A | 12/1996 | Kwun et al. | 73/623 |
| 5,814,982 A | 9/1998 | Thompson et al. | 324/171.1 |
| 5,854,557 A * | 12/1998 | Tiefnig | 324/700 |
| 5,888,374 A * | 3/1999 | Pope et al. | 205/775.5 |
| 6,077,418 A * | 6/2000 | Iseri et al. | 205/775.5 |
| 6,680,619 B1 * | 1/2004 | Horn | 324/700 |

OTHER PUBLICATIONS

M. Wang et al., *Modelling and Mapping Electrical Resistance Changes Due to Hearth Erosion in a 'Cold' Model of a Blast Furnace*, $1^{st}$ World Congress on Industrial Tomography, Apr. 14–17, 1999, pp. 161–166, XP002187994.

Roe Strommen et al., *FSM (Field Signature Method)—The New Technology for Internal Corrosion Monitoring of Pipelines, Vessels and Pressure Equipment*, Proceedings of the 1998 ASME Energy Sources Technology Conference, Houston Texas, Feb. 2–4, 1998, XP00105536.

Roe D. Strommen et al., *FSM–A Unique Method for Monitoring Corrosion of Steel Piping and Vessels*, N.A.C.E. Corrosion Asia Conference, Singapore, vol. 32, No. 4, Mar. 1993, pp. 50–55.

Roe D. Strommen et al., *New Technique Monitors Pipeline Corrosion, Cracking*, Oil & Gas Journal, vol. 91, No. 57, Dec. 27, 1993, pp. 88–92.

* cited by examiner

INVESTIGATING CORROSION

BACKGROUND OF THE INVENTION

1. Field of the Invention

This invention concerns improvements in and relating to investigating corrosion, particularly but not exclusively in relation to investigating corrosion in already corroded materials using field signature method based investigations.

2. Present State of the Art

The field signature method is based upon feeding a direct current through a location and measuring the electric field which is generated as a result using an array of electrical contacts on a surface of the location. Changes in the magnitude and shape of the electric field over time can provide significant information on corrosion occurring at the location.

To make measurements, an excitation current has to be applied to the location. The voltage across one or more pairs of contacts on the location to be measured and the voltage across one or more pairs of contacts on a non-corroding reference are measured repeatedly to monitor the corrosion that might be occurring.

Such techniques are known for monitoring future corrosion of new components. Generally speaking a pipeline to be monitored is installed and during its installation field signature measuring apparatus is provided for one or more short lengths of the pipeline. The electrodes used to measure the voltage are welded onto the surface of the pipeline to provide long monitoring lifetimes. Immediately on installation measurements are taken to establish the uncorroded voltage values for the various electrodes. These measurements form the base line values for subsequent measurements over the months and years as corrosion progresses.

Field signature methods to date are only available when provided with the location to be investigated when it is new and/or on the basis that any pre-existing corrosion is ignored and remains unquantified.

SUMMARY OF THE INVENTION

The present invention aims to extend the applicability of the technique to investigations on locations where corrosion may have or has already occurred.

According to a first aspect of the invention we provide a method of investigating corrosion at a location, the method including measuring the voltage between the two or more electrical contacts at one or more times, the two or more electrical contacts being in contact with a replica of the location being investigated, measuring the voltage between the two or more electrical contacts at a first time, the two or more electrical contacts being in contact with the location being investigated, a current being passed through the replica location at the time of the voltage measurement and through the location at the time of the voltage measurement, the voltage measurement for the replica location and for the location being considered to provide information about the corrosion which has occurred at the location.

The two or more electrical contacts may be provided on mounting means. The electrical contacts are preferably brought into contact with the replica of the location by introducing the mounting means to the replica location.

The replica location is preferably a replica which has not corroded. The replica location may be a replica whose corrosion is known.

Preferably the electrical contacts are brought into contact with the location by introducing the mounting means to the location. The location may have corroded.

Preferably the voltage between the two or more electrical contacts is measured at a first time and at one or more other times. The variation in voltage between two or more electrical contacts with time may be measured.

Preferably the current is provided by a given source for the replica location and location voltage measurements.

Preferably the voltage measurement for the replica location defines the characteristics for an uncorroded location, the voltage measurements for the location indicating the extent of corrosion which has occurred by the time of the first voltage measurement for the location and/or indicating the progress of corrosion between the first time and one or more of the other times of voltage measurement for the location.

According to a second aspect of the invention we provide a method of investigating corrosion at a location, the method including providing mounting unit for two or more electrical contacts, introducing the mounting unit to a replica of the location which has not corroded, measuring the voltage between the two or more electrical contacts a one or more times, the two or more electrical contacts being in contact with a replica of the location being investigated, introducing the mounting unit to the location which may have corroded, measuring the voltage between and/or the variation in the voltage between two or more electrical contacts at a first time and at one or more other times, the two or more electrical contacts being in contact with the location being investigated, passing a current through the replica location at the time of the voltage measurement and through the location at the time of the voltage measurements, the current being provided by a given source for the various voltage measurements the voltage measurement for the replica location defining the characteristics for an uncorroded location, the voltage measurements for the location indicating the extent of corrosion which has occurred by the time of the first voltage measurement for the location and/or indicating the progress of corrosion between the first time and one or more of the other times of voltage measurement for the location.

The first and/or second aspects of the invention may involve one or more of the following features, options or possibilities.

Corrosion may have already occurred at the location. Corrosion may have been occurring for more than a month and even more than a year before the first measurements for the location are taken. No previous measurement of the corrosion may have occurred before the time of the first measurement according to the present invention.

The corrosion investigated may occur throughout the location and/or at one or more specific parts of the location. The corrosion may occur due to contact between the location and its environment. The environment in question may be the external environment for the location and/or the internal environment for the location. The corrosion may arise as a result of chemical attack on the location and/or mechanical wear on the location. Corrosion may or may not have actually occurred at the time of the first voltage measurement for the location.

The location may be an entire article or a part there of. The location may particularly be a part of a chemical plant. The location may be a part or the whole of a pipeline, passageway, conduit, vessel, container, wall or barrier. The location may have one or more surfaces isolated from one or more other surfaces. The corrosion may effect one or more of the sets of isolated surfaces, for instance the internal surfaces in the case of a pipeline. The location may have been in use for sometime prior to the first voltage measurement. The location may be part of an existing plant when the first voltage measurements are made.

The electrical contacts may be provided by a mounting unit. The mounting unit is preferably provided with one or more surfaces configured to match one or more surfaces of the location to be investigated. Preferably the electrical contacts are provided on or associated with the one or more matching surfaces. One or more sections of the matching surface may be moveable relative to one or more of the other sections. Preferably at least three sections which are moveable relative to one another are provided.

The assembled mounting unit may be in the form of a ring and/or collar and/or provide an annular surface matching the surface of the location to be investigated, particularly where the location is a pipeline, conduit or other locations of circular or partially circular cross-section. The ring, collar or annular surface may be breakable to introduce the mounting unit around a location, particularly where the location is a pipeline, conduit or other locations of circular or partially circular cross-section.

Preferably all the electrical contacts are provided on a single mounting unit. Preferably the separation of two or more, ideally all, of the electrical contacts is fixed in one or more directions. The separation may be fixed in the first direction extending between one end of the mounting unit and the opposing end, for instance in the direction generally taken by the current flow in use. The separation may be fixed in a second direction, the second direction being perpendicular to the first, and preferably following the surface matching the location and/or following the location's surface. The electrical contacts may be moveably, for instance being spring loaded, perpendicular to the surface matching the location and/or perpendicular to the location's surface and/or perpendicular to both the first and second direction defined above.

The electrical contacts may be provided by pins or other electrically conducting elements. Preferably the electrical contacts are resiliently forced into contact with the location, for instance by springs. The electrical contacts may be provided in pairs, preferably with the voltage between predefined pairs being measured during the investigation. The electrical contacts and/or pairs of electrical contacts may be evenly spaced along the direction of current flow and/or perpendicular to the direction of current flow. Electrical contacts may be provided throughout the location, in the direction of current flow. The electrical contacts may be provided all around the cross-section of a pipeline or other form of conduit. The method may involve measuring the voltage for one or more pairs of electrical contacts simultaneously. Four or more and preferably eight or more pairs may be considered simultaneously. The number of pins provided may be between 8 and 256 pins, more preferably between 16 and 128 pins and ideally between 24 and 64 pins.

The mounting unit may be introduced to the replica location by causing the parts of the mounting unit which are brought into opposition with the location to approach the location. Preferably one or more, and ideally all, of the location opposing parts of the mounting unit are brought into opposition with the part of the location they oppose in use along an axis substantially perpendicular to the part of the location and/or such that the part of the mounting unit and part of the location are substantially parallel to one another. Substantially perpendicular and/or parallel preferably means at an angle thereto which does not result in scraping or other movement of the electrical contacts across the location between first contact therewith and reaching the position of use. The angle may be within 10° of the stated angle, or more preferably within 5° of the stated angle.

The mounting unit may be clamped or otherwise releasably fixed in position once introduced.

The method may provide for defining a base line characteristic or set of characteristics for the configuration of electrical contacts provided by the mounting unit, the method involving providing the mounting unit on a replica location and measuring the voltage for one or more pairs of electrical contacts to provide the base line characteristic or set of characteristics and further comprising transferring the mounting unit to the location, the voltage for one or more pairs of electrical contacts for which the voltage on the replica has been measured being measured. This method may be applied even where the replica does not exactly duplicate the location as even in such case the base line characteristic or set of characteristics for the mounting unit can be used together with the measurements for the location to give a measurement of localised corrosion for the location.

The replica location may replicate the location in terms of the material from which the location is formed and/or in terms of the thickness of material from which the location is formed and/or in terms of the shape of the location and/or in terms of the dimensions of the location and/or in terms of the components which form the location. Preferably the replica location is identical in all respects to the location before corrosion occurred and/or following introduction into its position of use and prior to use. The replica location may replicate the location based on records or other data on the location under investigation and/or estimates of the location under investigation.

A plurality of replica locations may be investigated. The replica locations may be the same replica location or a series of replica locations provided at a series of known extents of corrosion. The corrosion extents may represent various corrosion extents covering the range of corrosion extents which may have occurred for the location under investigation.

One or more voltage measurements and/or sets of voltage measurements may be taken for the replica location. Voltage measurements for the replica location may be undertaken before the location is considered and/or after the location is considered and/or intermediate considerations of the location. Preferably the replica location is protected against corrosion between measurements thereof.

Preferably each measurement of the replica location and/or the location is performed with the electrical contacts in the same position. The same positions may be defined relative to a reference point which remains fixed on or relative to the replica location and an equivalently positioned reference point fixed on or relative to the location and/or a constant orientation of the mounting unit on the replica location and location. Preferably each measurement of the replica location and/or of the location is performed with the mounting unit in the same position. Preferably the same position is defined relative to a reference point which remains fixed on or relative to the replica location and an equivalently positioned reference point fixed on or relative to the location.

The voltage measurements may indicate an evenly occurring electric field for all the respective electrical contacts considered for the replica location. The voltage measurements may indicate an unevenly occurring electric field for the replica location.

The voltage measurement for the replica may be made after the current has started. Preferably the voltage measurements are made at least 200 $ms^{-1}$ after the current has been applied. Preferably the voltage measurement is made within 800 $ms^{-1}$ of the current being applied. Preferably the voltage measurements are made after the current stops preferentially flowing in the surface part of the replica location. Preferably the voltage is steady when the voltage measurements are made.

The mounting unit may be introduced to the location in any of the ways of introducing it to the replica location defined above. Preferably the mounting unit is introduced to the location in an equivalent manner to its introduction to the replica location.

The voltage measurement for the location at the first time may be the same or higher as the voltage measured for the replica location. The voltage is preferably higher if corrosion has occurred by the time the first time of measurement. The difference between the voltage measured for the replica location and the voltage measured for the location may be proportional to the amount of corrosion which has occurred.

The variation in voltage may be an increase in voltage as corrosion progresses. The variation may occur evenly for all the respective electrical contacts considered. The variation may occur unevenly for all the respective electrical contacts considered. The variation may occur at an even rate over time. The variation may occur at an uneven rate over time. The variation may occur at an even rate around the cross-section of a pipeline or other conduit. The variation may occur at an uneven rate around the cross-section of a pipeline or other conduit.

The voltage measurements may be made after the current has started. Preferably the voltage measurements are made at least 200 $ms^{-1}$ after the current has been applied. Preferably the voltage measurement is made within 800 $ms^{-1}$ of the current being applied. Preferably the voltage measurements are made after the current stops preferentially flowing in the surface part of the location. Preferably the voltage is steady when the voltage measurements are made.

Preferably the temperature of the two or more electrical contacts is measured at one or more of the first time and/or one or more other times when the two or ore more electrical contacts are in contact with the location and/or replica location. Preferably the temperature is measured each time a voltage is measured for the location. Preferably the temperature is measured at each voltage measurement for the replica location. The temperature of the two or more electrical contacts may be measured by measuring the temperature of the electrical contacts. The temperature of the two or more electrical contacts and/or replica location may be measured by measuring the temperature of the location and/or the replica location. The temperature of the two or more electrical contacts may be measured by measuring the temperature of the environment surrounding the two or more electrical contacts when in contact with the location and/or the replica location.

Preferably the voltage measurements are compensated for temperature variations at the electrical contacts and/or location and/or replica location and/or reference location and/or the environment(s) thereof.

Preferably the method includes providing a power source external of the location to provide an applied current.

The current is preferably a DC current and particularly a square wave DC current. The DC current may be provided in a single direction but is more preferably applied in both directions, ideally alternately. The current may be applied for between 200 and 2000 $ms^{-1}$ per time and more preferably between 500 and 1000 $ms^{-1}$.

The current may be introduced to the replica location and/or location at one end thereof and leave at the other end thereof. The current may be introduced and/or exit by a current contact unit, preferably configured to match one or more surfaces of the replica location and/or location to be investigated or an element in electrical contact therewith. The current contact unit or units may be in the form of a ring, preferably a breakable ring, to investigate pipelines, conduits or other locations of circular or partially circular cross-section. The current contact unit or units may be in the form of a collar.

The power source may be a mains power source or portable power source, such as a battery. The power source may provide the same or a different current level for respective measurements.

The characteristics defined for the replica location by the voltage measurement may be a baseline voltage or voltages against which corrosion is considered and/or a thickness of material forming the replica location at one or more parts thereof and/or the shape of the electric field against which variations can be considered.

The voltage measurements for the location may indicate a general level of corrosion for the location, preferable through consistent variation between the various electrical contact voltages measured for the location and the baseline obtained from the replica. The voltage measurements for the location may indicate location specific corrosion for the location, preferably through inconsistent variation between the electrical contact voltages at one or more parts of the location and the baseline obtained from the replica and the electrical contact voltages at one or more other parts of the location and the baseline obtained from the replica. The corrosion may be expressed as a thickness loss, proportion of material lost or other value, such as a rate of loss. The corrosion may be expressed in terms of the change between the as new state represented by the replica location and the corroded state of the first measurement time and/or in terms of the progress of corrosion from the first time onwards.

Variations in the current may be accounted for using the process or apparatus disclosed in U.S. Publication No. 2003/0184322, published Oct. 2, 2003.

The method may provide for passing the applied current through a reference location and measuring the variation in the voltage between two or more reference electrical contacts at the first time and at one or more of the one or more other times, the two or more reference electrical contacts being in contact with the reference location. In this way variations in the current provided by the power supply may be accounted for between measurements.

Preferably the temperature of the reference location is measured each time a voltage is measured for the location. Preferably the temperature of the reference location is measured each time a voltage is measured for the replica location. The temperature of the reference location may be measured by measuring the temperature of the reference location. The temperature of the reference location may be measured by measuring the temperature of the environment surrounding the reference location.

Preferably the method provides for using the respective voltage values from the two or more electrical contacts and two or more reference electrical contacts in the investigation of the corrosion.

The reference location is preferably between the power source and the location in an electrical sense. The reference location is preferably formed of a material which does not corrode in its environment. The environment may be different from the environment effecting the location under investigation. The reference location may be provided with only two electrical contacts. The reference location may be physically distant from the location under investigation.

The voltage for the reference location at a measurement time may be used to compensate one or more voltages measured for the location or a part thereof for variations in the applied current at one measurement time and one or more other measurement times. Preferably the compensation is made according to the equation:

$$Fc_{Ai} = \frac{B_s}{A_s} \times \frac{A_i}{B_i} - 1 \times 1000 \text{ (parts per thousand)}$$

where
$Fc_{Ai}$=fingerprint coefficient for a pair of electrical contacts A under investigation at time i;
$A_s$=voltage across pair A when on the replica;
$B_s$=voltage across reference pair of electrical contacts B when on the replica;
$A_i$=voltage across pair A on location at time i;
$B_i$=voltage across reference pair B at time i.

According to a third aspect of the invention we provide apparatus for investigating corrosion at a location, the apparatus including one or more replicas of the location two or more electrical contacts in contact with the replica location during measurements thereof and in contact with the location during measurements thereof, means for measuring the voltage between the two or more electrical contacts in contact with the replica location, means for measuring the voltage between the two or more electrical contacts in contact with the location at a first time, a power source for passing a current through the replica location and the location at the respective times of the voltage measurements, means for considering the voltage measurements from the replica location and the location being considered to provide information about the corrosion which has occurred at the location.

According to a fourth aspect of the invention we provide apparatus for investigating corrosion at a location, the apparatus including one or more replicas of the location, at least one of which has not corroded, A mounting unit for two or more electrical contacts, the two or more electrical contacts being in contact with a replica location during measurements thereof and in contact with the location during measurements thereof, means for measuring the voltage between the two or more electrical contacts in contact with the replica location, means for measuring the voltage between and/or the variation in the voltage between the two or more electrical contacts at a first time and at one or more other times, a power source for passing a current through the replica location and through the location at the respective times of the voltage measurements, means for defining the characteristics of an uncorroded location from the voltage measurements of the replica location, and means for indicating the extent of corrosion which has occurred at the first time for the location and/or indicating the progress of corrosion between the first and one or more other times of voltage measurement for the location.

The third and/or fourth aspects of the invention may include any of the features, options or possibilities set out in this document, including means for their implementation.

The electrical contacts may be provided by an electrical contact mounting unit. A mounting unit is preferably configured to match one or more surfaces of the location to be investigated. The mounting unit may be in the form of a ring, preferably a breakable ring. The mounting unit may be in the form of a partial ring. The mounting unit may be in the form of a collar.

The electrical contact may be provided by pins or other electrically conducting elements, preferably mounted on the mounting unit. Preferably the electrical contacts are resiliently biased, ideally towards the location in use. The electrical contact may be biased by springs. The electrical contacts are preferably provided in pairs. The electrical contact and/or pairs of electrical contacts may be evenly spaced along the mounting unit.

Preferably the current is introduced by an external power source. A mains power source or portable power source, such as a battery, may be used.

The apparatus may include beams for introducing the current to one part of the location and removing the current from another part of the location. The means may comprise a current contact unit, preferably configured to match one or more surfaces of the location to be investigated and/or an element in electrical contact with one or more surfaces of the location to be investigated. The current contact unit or units may be in the form of a ring, preferably a breakable ring. The current contact unit or units may be in the form of a partial ring and/or collar.

The non-intrusive current measuring means may be configured to match one or more surfaces of the location. The non-intrusive current measuring means may be in the form of a ring, preferably a breakable ring. The non-intrusive current measuring means may be in the form of a collar and/or partial ring.

The Hall effect current measuring means may be provided by a semi-conductor material with an applied constant current passing through it in a first direction. The first direction is preferably configured to be substantially, and ideally to be, perpendicular to the direction of the magnetic field, the second direction, generated by the current passing through the location. The Hall effect may be measured by measuring the Hall voltage. The Hall effect may be measured by measuring a voltage arising across the semi-conductor, preferably substantially perpendicular to the first and second direction, ideally perpendicular to both directions. The Hall effect current measuring means may be one or more Hall effect transducers.

The apparatus may further include a reference location electrically connected to the power source. Preferably the reference location is provided between the power source and a current contact unit and/or the location. The reference location is preferably provided with two or more reference electrical contacts.

BRIEF DESCRIPTION OF THE DRAWINGS

Various embodiments of the invention will now be described, by way of example only, with reference to the accompanying drawings in which.

DETAILED DESCRIPTION OF THE PREFERRED EMBODIMENTS

Figure 1:
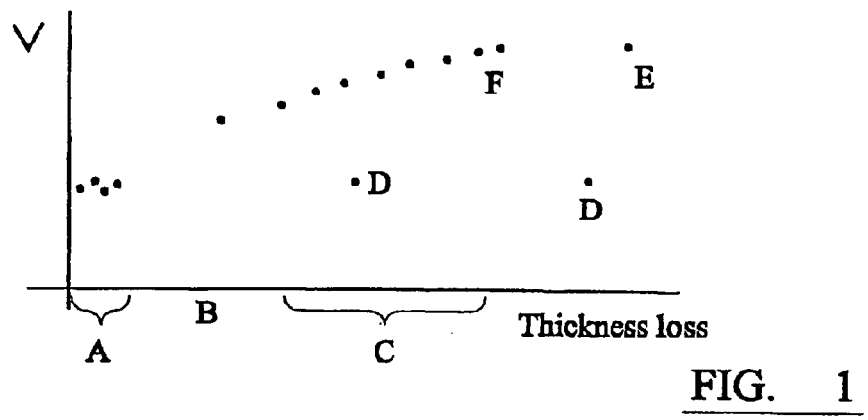
FIG. 1 illustrates schematically the results of measurements conducted on an uncorroded sample and on a potentially corroded sample using the technique of the present invention.

When ever an electric current is passed through a location an electric field is generated. The material, thickness of material, shape and configuration of the location effect the size and shape of the electric field that results. Changes in one or more of these potential variables effects the electric field. In particular, corrosion of a location, such as a pipeline, generally reduces the thickness of material, increases the resistance and hence the voltage drop between different positions along the location in the direction of current flow.

The field effect method makes use of this basic principal to provide information on corrosion. The method applies an excitation current to the location under consideration for a short time period, fractions of a second, and measures the voltage drops between a large number of different pairs of electrical contacts touching the location. By considering the results the progress of corrosion can be evaluated. In general the results are considered in terms of a fingerprint coefficient for a given pair of electrical contacts with time, particularly according to the formula:

$$Fc_{Ai} = \frac{B_s}{A_s} \times \frac{A_i}{B_i} - 1 \times 1000 \text{ (parts per thousand)}$$

where $Fc_{Ai}$=fingerprint coefficient for electrode pair A at time I
$A_s$=voltage across pair A at start
$B_s$=voltage across reference pair B at start
$A_i$=voltage across pair A at time I
$B_i$=voltage across reference pair B at time I The reference pair of electrodes being provided on a non-corroding material through which the excitation current passes on its way to the location. This feature is generally employed so that variations between measurement in the current provided by the power supply do not effect the measurements.

Information on general corrosion due to a general variation in the field over time can be investigated and monitored and/or localised corrosion can be investigated and monitored where variations occur for only some of the pairs of electrical contacts.

As is clear from the terms of the formula above the technique is only employed at present on locations for which corrosion investigations are carried out from new and for which, as a result, uncorroded voltage measurements are made. Alternatively pre-existing corrosion is ignore and remains unquantified.

The present invention extends this range of uses for field signature methods by enabling the methods to be applied successfully to locations for which corrosion to an unknown level or extent may have already occurred.

To achieve this aim as much information as possible about the location to be investigated is sought. For all active process plant and other situations where the technique might be applied the material from which the location is made and the original thickness of the material forming the location is also known. The configuration of the location, be it a simple length of circular cross-sectioned pipe or more complicated pipe with T junction and valve unit, is also known or can be derived from external inspection.

Based on this information a replica of the location to be investigated can be bought, otherwise obtained or constructed. This uncorroded replica can then be subjected to voltage measurements using field signature apparatus. The voltage results obtained for the various pairs of electrical contacts are recorded in one or more measurement runs. Four measurements for a single pair of pins, set A, are shown in FIG. 1.

Once this process has been performed the same field signature apparatus is taken and installed at the location to be investigated. Once placed in exactly the same position as was used on the replica location, using some standard reference point to both, the voltage measurements can be started, value B for the single pair of pins again shown in FIG. 1.

The field signature method is then used to monitor the location over time as corrosion progresses and the voltage rises as a result, set of values C in FIG. 1.

The extent of corrosion relative to new can then be considered, ideally compensated according to the equation:

$$Fc_{Ai} = \frac{B_s}{A_s} \times \frac{A_i}{B_i} - 1 \times 1000 \text{ (parts per thousand)}$$

where $Fc_{Ai}$=fingerprint coefficient for a pair of electrical contacts A under investigation at time i;
$A_s$=voltage across pair A when on the replica;
$B_s$=voltage across reference pair of electrical contacts B when on the replica;
$A_i$=voltage across pair A on location at time i;
$B_i$=voltage across reference pair B at time i.

It would be possible to periodically remove the apparatus and returned to the replica location and take measurements. These values, points D in FIG. 1, should correspond in value to set A as no corrosion occurs for the replica location. Upon return to the corroding location once more the correct positioning, consistent with the previous position is confirmed by the value measured, point E in FIG. 1, corresponding to the value, point F in FIG. 1, measured just before removal (the rate of corrosion being such that no change occurs in the relatively short time needed to remove and reinstall the apparatus). Such a technique might be useful where confirmation of the continued accurate measurement of the apparatus is needed and/or a large number of location were under consideration by a single apparatus set.

Even this information provides significant information about the rate and extent of corrosion occurring, whether that be in a general sense or location specific sense.

The present invention also allows for a more immediate consideration of the extent of corrosion which has occurred in the unknown corroded location from the measurements of it. By effectively generating replica corroded locations of varying extents and performing measurements on these the effect of the progression of corrosion can established. Typical results are set out in set Z of FIG. 2. This type of result can be achieve by gradually progressing the corrosion on a single replica, using it for the new and increasingly corroded measurements, or by using a series of replicas which are advanced to various corrosion levels, predominantly losses of thickness of material. The corroded replicas are formed under corresponding but accelerated corrosion conditions.

Figure 2:
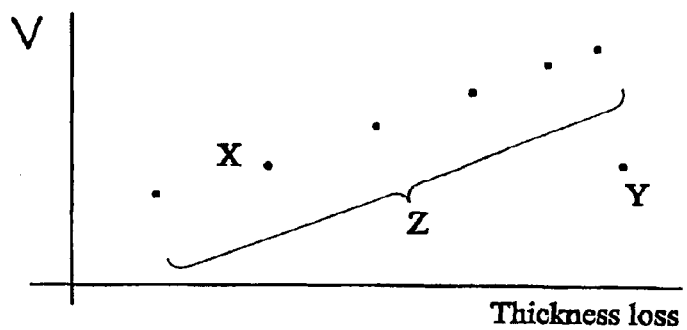
FIG. 2 illustrates schematically a comparison of the measurement obtained for the unknown corroded sample of FIG. 1 compared with measurements for a number of samples of known corrosion levels.

These results can immediately be compared with the measurements made for the unknown corroded location. As shown in FIG. 2 the unknown location gives a value point Y generally with the level measured for point X of the replica corroded locations thereby suggesting a matching corrosion level.

Figure 3:
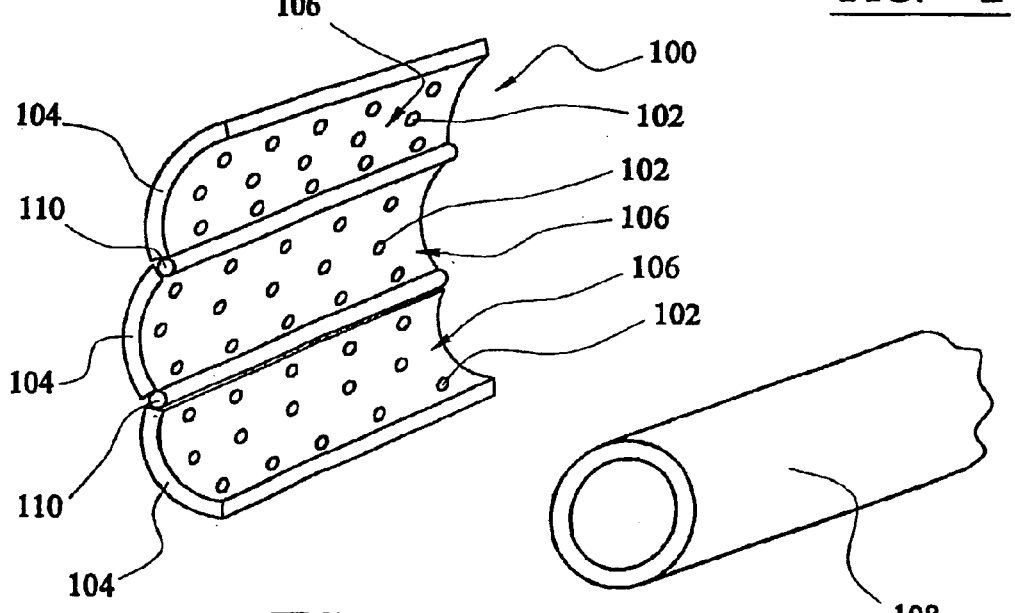
FIG. 3 illustrates an embodiment of a sensing head suitable for implementing the present invention.

To enable a replica location and actual location to be considered alongside one another in a meaningful manner it is important that the electrical contacts are provided in a consistent set of positions on each. To this end a set of apparatus as described below and as exemplified in FIG. 3 when used on a pipeline is preferred.

The apparatus illustrated is merely the mounting unit 100 for the electrical contacts 102. The mounting unit is formed of three separate portions 104 each of which have a curved inner surface 106 together forming a full circle of the same general shape as the pipeline 108 on which it is intended to use the unit 100. Bach of the inner surfaces 106 is punctuated with a regular pattern of holes each of which contains a metal pin which forms the electrical contact 102. The pins are spring loaded in the holes and have a sharp point to assist in making good electrical contact with the outside of the pipeline 108.

The unit 100 is provided in three portions 104 so as to allow it to be easily introduced to the pipeline 108 by wrapping it around the pipeline 108. The three portion form is far better than a two portion form as the protruding pins are not scraped across the surface of the pipeline 108 during assembly of the unit 100 in the case of a three or more portion form. Any scraping risks breaking the pins or altering their positions with detrimental results on the measurements. The three portions 104 are joined to one another by hinges.

As the positions of all the pins are fixed relative to one another they are always introduced to a location, be it a replica location or the actual location in a consistent manner. If the pins or sets of pins could move relative to one another then the measurements would not be comparable with one another.

Other mounting unit configurations can of course be provided for other location configurations following the same general principle.

What is claimed is:

1. A method of investigating corrosion at a location, the method comprising:

providing a mounting unit for two or more electrical contacts, introducing the mounting unit to a replica location, the replica location being a non-corroded replica of the location being investigated, measuring the voltage between the two or more electrical contacts at one or more times, the two or more electrical contacts being in contact with the replica location, introducing the mounting unit to the location being investigated which may have corroded, measuring the voltage between and/or the variation in the voltage between two or more electrical contacts at a first time and at one or more other times, the two or more electrical contacts being in contact with the location being investigated, and passing a current through the replica location at the time of the voltage measurement and through the location being investigated at the time of the voltage measurements, the current being provided by a given source for the various voltage measurements, the voltage measurement for the replica location defining the characteristics for an uncorroded location, and the voltage measurements for the location being investigated indicating the extent of corrosion which has occurred by the time of the first voltage measurement for the location being investigated and/or indicating the progress of corrosion between the first time and one or more of the other times of voltage measurement for the location being investigated.

2. A method of investigating corrosion at a location, the method comprising:

measuring the voltage between the two or more electrical contacts at one or more times, the two or more electrical contacts being in contact with a replica location, the replica location being a non-corroded replica of the location being investigated, measuring the voltage between the two or more electrical contacts at a first time, the two or more electrical contacts being in contact with the location being investigated, a current being passed through the replica location at the time of the voltage measurement and through the location at the time of the voltage measurement, the voltage measurement for the replica location and for the location being investigated to provide information about the corrosion, which has occurred at the location, in which the voltage measurement for the replica location defines the characteristics for an uncorroded location, the voltage measurements for the location being investigated indicating the extent of corrosion which has occurred by the time of the first voltage measurement for the location being investigated and/or indicating the progress of corrosion between the first time and one or more of the other times of voltage measurement for the location being investigated.

3. A method according to claim 2 in which the two or more electrical contacts are provided on mounting means, the electrical contacts are preferably brought into contact with the replica location by introducing the mounting means to the replica location, and the electrical contacts being brought into contact with the location being investigated by introducing the mounting means to the location being investigated.

4. A method according to claim 2 in which the method provides for defining a base line characteristic or set of characteristics for the configuration of electrical contacts provided by the mounting means, the method comprising:

providing the mounting means on a replica location and measuring the voltage for one or more pairs of electrical contacts to provide the base line characteristic or set of characteristics, and transferring the mounting means to the location being investigated, and measuring the voltage for one or more pairs of electrical contacts for which the voltage on the replica location has been measured, and providing information about localised corrosion for the location being investigated based on differences between the voltages measured for the location being investigated over time compared with the base line characteristic or set of characteristics.

5. A method according to claim 2 in which the replica location replicates the location being investigated in terms of at least one of the material, the thickness of material, the shape, the dimensions, and the components which form the location being investigated.

6. A method according to claim 2 in which the replica location is identical in all respects to the location being investigated before corrosion occurred and/or following introduction into its position of use and prior to use.

7. A method according to claim 2 in which a plurality of replica locations are investigated, the replica locations being the same replica location or a series of replica locations provided at a series of known extents of corrosion.

8. A method according to claim 2 in which each measurement of the replica location and/or location being investigated is performed with the mounting unit in the same position.

9. A method according to claim 2 in which each measurement of the replica location and/or location being investigated is performed with the electrical contacts in the same position.

10. A method according to claim 2 in which the mounting unit is introduced to the replica location and/or location being investigated by causing the parts of the mounting unit which are brought into opposition with the replica location and/or location being investigated to approach the replica location and/or location being investigated, one or more of the replica location and/or location being investigated opposing parts of the mounting unit being brought into opposition with the part of the replica location and/or location being investigated they oppose in use along an axis substantially perpendicular to the part of the replica location and/or location being investigated and/or such that the part of the mounting unit and part of the replica location and/or location being investigated are substantially parallel to one another.

11. A method according to claim 1 in which the two or more electrical contacts are provided on mounting means, the electrical contacts are preferably brought into contact with the replica location by introducing the mounting means to the replica location, and the electrical contacts being brought into contact with the location being investigated by introducing the mounting means to the location being investigated.

12. A method according to claim 1 in which the voltage measurement for the replica location defines the characteristics for an uncorroded location, the voltage measurements for the location being investigated indicating the extent of corrosion which has occurred by the time of the first voltage measurement for the location being investigated and/or indicating the progress of corrosion between the first time and one or more of the other times of voltage measurement for the location being investigated.

13. A method according to claim 1 in which the method provides for defining a base line characteristic or set of characteristics for the configuration of electrical contacts provided by the mounting means, the method comprising:
   providing the mounting means on a replica location and measuring the voltage for one or more pairs of electrical contacts to provide the base line characteristic or set of characteristics, and
   transferring the mounting means to the location being investigated, and measuring the voltage for one or more pairs of electrical contacts for which the voltage on the replica location has been measured, and
   providing information about localised corrosion for the location being investigated based on differences between the voltages measured for the location being investigated over time compared with the base line characteristic or set of characteristics.

14. A method according to claim 1 in which the replica location replicates the location being investigated in terms of at least one of the material, the thickness of material, the shape, the dimensions, and the components which form the location being investigated.

15. A method according to claim 1 in which the replica location is identical in all respects to the location being investigated before corrosion occurred and/or following introduction into its position of use and prior to use.

16. A method according to claim 1 in which a plurality of replica locations are investigated, the replica locations being the same replica location or a series of replica locations provided at a series of known extents of corrosion.

17. A method according to claim 1 in which each measurement of the replica location and/or location being investigated is performed with the mounting unit in the same position.

18. A method according to claim 1 in which each measurement of the replica location and/or location being investigated is performed with the electrical contacts in the same position.

19. A method according to claim 1 in which the mounting unit is introduced to the replica location and/or location being investigated by causing the parts of the mounting unit which are brought into opposition with the replica location and/or location being investigated to approach the replica location and/or location being investigated, one or more of the replica location and/or location being investigated opposing parts of the mounting unit being brought into opposition with the part of the replica location and/or location being investigated they oppose in use along an axis substantially perpendicular to the part of the replica location and/or location being investigated and/or such that the part of the mounting unit and part of the replica location and/or location being investigated are substantially parallel to one another.

20. Apparatus for investigating corrosion at a location, the apparatus comprising one or more replicas of the location being investigated, at least one of which has not corroded,
   a mounting unit for two of more electrical contacts, the two or more electrical contacts being in contact with a replica location during measurements thereof and in contact with the location being investigated during measurements thereof,
   means for measuring the voltage between the two or more electrical contacts in contact with the replica location,
   means for measuring the voltage between and/or the variation in the voltage between the two or more electrical contacts at a first time and at one or more other times,
   a power source for passing a current through the replica location and through the location being investigated at the respective times of the voltage measurements,
   means for defining the characteristics of an uncorroded location from the voltage measurements of the replica location, and
   means for indicating the extent of corrosion which has occurred at the first time for the location being investigated and/or indicating the progress of corrosion between the first and one or more other times of voltage measurement for the location being investigated.

21. Apparatus according to claim 20 in which the electrical contacts are provided by a mounting unit, the mounting unit being provided with one or more surfaces configured to match one or more surfaces of the replica location and/or location being investigated, the electrical contacts being provided on or associated with the one or more matching surfaces.

22. Apparatus according to claim 20 in which the assembled mounting unit is in the form of a ring and/or collar and/or provide an annular surface matching the surface of the replica location and/or location being investigated.

23. Apparatus according to claim 22 in which the ring, collar or annular surface is breakable to introduce the mounting unit around replica location and/or location being investigated.

24. Apparatus according to claim 20 in which the separation of two or more of the electrical contacts is fixed in one or more directions.

* * * * *